United States Patent [19]

De Lacharriere et al.

[11] Patent Number: 5,858,024
[45] Date of Patent: Jan. 12, 1999

[54] COMPOSITION FOR DYEING KERATIN FIBRES CONTAINING A SUBSTANCE P ANTAGONIST

[75] Inventors: Olivier De Lacharriere, Paris; Lionel Breton, Versailles; Genevieve Loussouarn, Clichy, all of France

[73] Assignee: Société L'Oréal S.A., Paris, France

[21] Appl. No.: 716,534

[22] Filed: Sep. 19, 1996

[30] Foreign Application Priority Data

Sep. 19, 1995 [FR] France .................................. 95-10979

[51] Int. Cl.⁶ ........................................................ A61K 7/13
[52] U.S. Cl. .......................... 8/408; 8/405; 8/406; 8/407; 8/423; 8/563; 8/618; 8/637.1; 424/70.6
[58] Field of Search ................... 8/405, 406, 407, 8/408, 409, 410, 411, 412, 414, 425, 426, 564, 563, 565, 568, 570, 574, 623, 620, 637.1, 662, 618, 423; 424/70.6

[56] References Cited

U.S. PATENT DOCUMENTS

| | | | |
|---|---|---|---|
| 3,772,431 | 11/1973 | Milkvy et al. | 424/44 |
| 3,861,868 | 1/1975 | Milbrada | 8/410 |
| 3,888,976 | 6/1975 | Milkvy et al. | 424/44 |
| 3,960,476 | 6/1976 | Ghilardi et al. | 8/524 |
| 4,314,810 | 2/1982 | Fourcadier et al. | 8/410 |
| 4,447,439 | 5/1984 | D'Alelio | 424/162 |
| 4,710,374 | 12/1987 | Grollier et al. | 8/405 |
| 4,749,565 | 6/1988 | Grollier et al. | 8/405 |
| 4,801,302 | 1/1989 | Grollier et al. | 8/429 |
| 4,933,177 | 6/1990 | Grollier et al. | 8/425 |
| 4,943,432 | 7/1990 | Biener | 424/647 |
| 4,971,596 | 11/1990 | Grollier | 8/425 |
| 4,980,154 | 12/1990 | Gordon | 424/53 |
| 4,981,485 | 1/1991 | Motono | 8/405 |
| 4,986,981 | 1/1991 | Glace et al. | 424/50 |
| 4,992,077 | 2/1991 | Tennigkeit et al. | 8/406 |
| 5,006,127 | 4/1991 | Tennigkeit et al. | 8/406 |
| 5,008,105 | 4/1991 | Grollier et al. | 8/405 |
| 5,047,409 | 9/1991 | Di Schiena et al. | 514/275 |
| 5,079,010 | 1/1992 | Natterer | 424/617 |
| 5,091,171 | 2/1992 | Yu et al. | 424/624 |
| 5,202,130 | 4/1993 | Grant et al. | 424/617 |
| 5,368,610 | 11/1994 | Chan et al. | 8/406 |
| 5,447,538 | 9/1995 | Rosenbaum et al. | 8/405 |
| 5,474,578 | 12/1995 | Chan et al. | 8/431 |
| 5,520,707 | 5/1996 | Lim et al. | 8/425 |
| 5,569,662 | 10/1996 | Satake et al. | 514/305 |
| 5,609,650 | 3/1997 | Knuebel et al. | 8/406 |
| 5,716,625 | 2/1998 | Hahn et al. | 424/401 |

FOREIGN PATENT DOCUMENTS

| | | |
|---|---|---|
| 0217975 | 4/1987 | European Pat. Off. . |
| 0401503 | 4/1990 | European Pat. Off. . |
| 0439640 | 8/1991 | European Pat. Off. . |
| 0459890 | 12/1991 | European Pat. Off. . |
| 0522808 | 7/1992 | European Pat. Off. . |
| 0586929 | 3/1994 | European Pat. Off. . |
| 0612525 | 8/1994 | European Pat. Off. . |
| 0680749 | 11/1995 | European Pat. Off. . |
| 5394 | 10/1967 | France . |
| 2184890 | 6/1978 | France . |
| 3338957 | 5/1985 | Germany . |
| 297 062 | 1/1992 | Germany . |
| 2271774 | 4/1994 | United Kingdom . |
| WO 83/01252 | 4/1983 | WIPO . |
| WO 87/01935 | 4/1987 | WIPO . |
| WO 93/01165 | 1/1993 | WIPO . |
| WO 93/14084 | 7/1993 | WIPO . |
| WO 96/19184 | 6/1996 | WIPO . |

OTHER PUBLICATIONS

S.M. Moussaoui et al, *Br. J. Pharmacol.*, "A non–peptide $NK_1$–receptor antagonist, RP 67580, inhibits neurogenic inflammation postsynaptically", vol. 109, No. 1, 1993, pp. 259–265 (no month available).

J. Wallengren, *Br. J. Dermatol.*, "Substance P antagonist inhibits immediate and delayed type cutaneous hypersensitivity reactions", vol. 124, No. 4, 1991, pp. 324–328 (no mo. avail.).

J. Wallengren et al. *Contact Dermatitis*, "Some neuropeptides as modulators of experimental contact allergy", vol. 19, No. 5, 1988, pp. 351–354 (no month available).

T. Lotti et al, *J. Am. Acad. Dermatol.*, "Treatment of aquagenic pruritus with topical capsaicin cream", vol. 30, No. 2PT1, Feb. 1994, pp. 232–235.

T. Sakurada et al, *Brain Res.*, "A selective and extremely potent antagonist of the neurokinin–1 receptor", vol. 593, No. 2, 1992, pp. 319–322 ( no month available).

K. Folkers et al, *Proc. Natl. Acad. Sci. USA*, "Spantide II, an effective tachykinin antagonist having high potency", vol. 87, No. 12, 1990, pp. 4833–4855 (no month available).

Rajadhyaksha, Chemical Abstracts, vol. 107, #223281, Dec. 1987.

Smith et al., Chemical Abstracts, vol. 114, #206554, May 1991.

Dufetel et al., Chemical Abstracts, vol. 116, Apr. 1992, #135998.

Jancso–Gabor, "Action of rare earth metal complexes on neurogenic as well as on bradykinin–induced inflammation", *J. Pharm. Pharmac.*, 22:366–371 (1970)(no month available).

"La peau sensible, un authentique syndrome clinique", *Le Quotidien du Medecin*, No. 5747, Dec. 6, 1995.

Cosmetologie, *Therapeutique*, No. 1511, Dec. 17, 1995.

(List continued on next page.)

*Primary Examiner*—Paul Lieberman
*Assistant Examiner*—Caroline L. Dusheck
*Attorney, Agent, or Firm*—Burns, Doane, Swecker & Mathis, L.L.P.

[57] ABSTRACT

The invention relates to a composition, in particular a cosmetic composition, and more particularly one for dyeing keratin fibers, this composition containing at least one substance P antagonist in order to reduce or even eliminate the irritant effects of the dyes and/or pigments and/or dye precursors used during this dyeing. The substance P antagonist may form part of the dye composition itself or may be contained in a composition which is applied prior to the application of the dye composition.

21 Claims, No Drawings

OTHER PUBLICATIONS

Uy Dong SOHN et al, "Agonist–Independent, Muscle–Type–Specific Signal Transduction Pathways in Cat Esophageal and Lower Esophageal Sphincter Circular Smooth Muscle", *J. of Pharmacology & Experimental Therapeutics*, 273:481–491 (1995)(no month available).

Mitsuo Ishizawa, "Contractile Responses of Longitudinal Muscle Strip of 5–HT and Influences of Divalent Cations in the Guinea–Pig Isolated Colon", *J. Smooth Muscle Res.*, 30:65–72, (Apr. 1994).

H. Goodman, *Cosmetic Dermatology*, First Edition, Fourth Impression, p. 181 (1936) (no month available).

*Martindale*, The Extra Pharmacopoeia, Twenty–seventh Edition, The Pharmaceutical Press, London, pp. 219, 1775 and 1814 (1977) (no month available).

Sohn et al, Different Receptors Activate a Different Single G–Protein in Esophageal. (Gis) and in LES (Gq) Circular Smooth Muscle, *Gastroenterology*, vol. 104, Apr. 1993.

Maison G. deNavarre, *The Chemistry and Manufacture of Cosmetics*, 2nd Ed. vol. IV, p. 1261 (1975) (no month available).

Alexander A. Fisher, "Irritant Reactions from Topical Urea Preparations Used for Dry Skin Advantages of a Urea–Free 'Dead Sea Salt' Cream", *Current Contact News*, vol. 18, pp. 761–772, Dec., 1976.

*The United States Pharmacopeia*, "Alumina/Drug Substances and Dosage Form", pp. 20 and 22, Jul., 1975.

*Nordia Briefs*, "A Salt–Containing Cream for Dry Skin", No. 484, Jan. 1978.

*Cosmetic Counter*, vol. 109, Oct. 1994, p. 15.

Database WPI, Week 9216; Derwent Publications Ltd., London, GB; AN 92–127243 (abstract of JP–A–04 069 324 Mar. 4, 1992).

Database WPI, Week 9013; Derwent Publications Ltd., London, GB; AN 90096015 (abstract of JP–A–02 048 519, Feb. 19, 1990).

COMPOSITION FOR DYEING KERATIN FIBRES CONTAINING A SUBSTANCE P ANTAGONIST

BACKGROUND OF THE INVENTION

Technical Field of the Invention

The present invention relates to a composition, in particular a cosmetic composition, and more particularly one for dyeing keratin fibres, this composition containing at least one substance P antagonist in order to reduce or even eliminate the irritant effects of dyes and/or pigments and/or dye precursors contained in such a composition. The invention also relates to a process for dyeing keratin fibres.

Two main types of dyeing of keratin fibres exist: direct dyeing using direct dyes and/or pigments which are coloured molecules that give the fibres a temporary colour which fades after shampooing a few times, and dyeing known as "oxidation dyeing" using oxidation dye precursors and an oxidizing agent which gives the fibres a fast colour.

These two types of dyeing require the application onto the keratin fibres of compositions containing, in a support which is suitable for dyeing, the various direct dyes and/or pigments and/or oxidation dye precursors in the presence of an oxidizing agent.

These dyes, pigments and dye precursors may result in irritations, in particular in certain people, and this irritant effect is experienced all the more by a treated individual if he or she has a sensitive scalp.

The Applicant has discovered that the use of substance P antagonists makes it possible to obtain a preventive and/or curative effect on the irritation caused by dyes, pigments and/or dye precursors.

Substance P is a polypeptide chemical element which is produced and released by nerve endings. It forms part of the family of tachykinins. Substance P is involved in particular in the transmission of pain and in illnesses of the central nervous system such as anxiety and schizophrenia, in respiratory and inflammatory diseases, in gastrointestinal diseases, in rheumatic diseases and in certain dermatological diseases such as eczema.

To date, nobody had envisaged using substance P antagonists in prior application before a dyeing operating or in combination with dyestuffs so as to eliminate the irritant effect of the latter.

Thus, the subject of the present invention is a composition, in particular a cosmetic composition, containing, in a cosmetically acceptable medium, at least one substance P antagonist and at least one active agent with an irritant side effect, characterized in that the active agent with an irritant side effect is a dye, a pigment and/or a dye precursor.

The composition according to the invention is especially a composition for dyeing keratin fibres and, in particular, a composition for dyeing human hair.

Thus, the subject of the present invention is also a composition for dyeing keratin fibres which contains, in a medium which is suitable for dyeing, a dye, a pigment and/or a dye precursor with an irritant side effect, characterized in that it also contains at least one substance P antagonist.

The substance P antagonist may be found in the dye composition itself or in a composition applied to the keratin fibres before the application of the dye composition.

Consequently, the subject of the present invention is also a product for dyeing keratin fibres, which comprises a first composition containing at least one substance P antagonist and a second composition containing, in a medium which is suitable for dyeing, a dye, a pigment and/or a dye precursor with an irritant side effect, the two compositions being intended to be applied one after the other.

According to a particular embodiment of the invention, the first and the second compositions are packaged separately in the form of a kit, in an arrangement which is well known to those skilled in the art, in particular in the pharmaceutical field.

Thus, the subject of the present invention is also a kit for dyeing keratin fibres and in particular human keratin fibres such as the hair, which comprises a first composition containing at least one substance P antagonist and a second composition containing, in a medium which is suitable for dyeing, a dye, a pigment and/or a dye precursor with an irritant side effect, the two compositions, intended to be applied one after the other, being packaged separately.

The subject of the present invention is also a process for dyeing keratin fibres and in particular human keratin fibres such as the hair, characterized in that a composition containing at least one substance P antagonist and at least one dye, one pigment and/or one dye precursor with an irritant side effect, in a medium which is suitable for dyeing, is applied to the fibres.

The subject of the present invention is also a process for dyeing keratin fibres and in particular human keratin fibres such as the hair, characterized in that a first composition containing at least one substance p antagonist is applied to the fibres, followed by a second composition containing at least one dye, one pigment and/or one dye precursor with an irritant side effect, in a medium which is suitable for dyeing.

The second composition is applied to the keratin fibres a certain time after application of the first composition, this time interval advantageously being from 5 to 10 minutes.

In order for a substance to be recognized as a substance P antagonist, it must satisfy the following characteristic:

it must have a substance P-antagonist pharmacological activity, that is to say induce a coherent pharmacological response in at least one of the following two tests:

the antagonist substance must decrease the extravasation of plasma across the vascular wall induced by capsaicin or by antidromic nerve stimulation, or alternatively the antagonist substance must give rise to an inhibition of the contraction of smooth muscle induced by the administration of substance P.

The substance P antagonist may also have a selective affinity for tachykinin NK1 receptors.

The substance P antagonist of the invention may be functional or receptorial, that is to say that it may inhibit the synthesis and/or release of substance P, or prevent its binding and/or modify its action. It may be chosen from compounds known as substance P antagonists, in particular peptides or nitrogenous, non-peptide derivatives, and more particularly those containing a nitrogenous heterocycle or a nitrogen atom linked directly or indirectly to a benzene ring, cobalt salts, neodymium salts, and salts of the elements of column II A of the Periodic Table. It may also be chosen from extracts of plant and/or bacterial origin.

Thus, sendide and spantide II may be used in the invention, for example, as peptide antagonist of substance P.

Sendide corresponds to the formula:

Tyr D-Phe Phe D-His Leu Met $NH_2$ in which:

Tyr represents tyrosine,

D-Phe represents D-phenylalanine,

Phe represents phenylalanine,

D-His represents D-histidine,
Leu represents leucine,
Met represents methionine.

Spantide II corresponds to the formula:
D-LysNic Pro 3-Pal Pro D-Cl$_2$Phe Asn D-Trp Phe D-Trp Leu Nle NH$_2$ in which:
D-LysNic represents D-lysine nicotinate,
Pro represents proline,
3-Pal represents 3-pyridylalanine,
D-Cl$_2$Phe represents D-dichlorophenylalanine,
Asn represents asparagine,
D-Trp represents D-tryptophan,
Phe represents phenylalanine,
Leu represents leucine,
Nle represents norleucine.

The peptides described in the documents U.S. Pat. No. 4,472,305, U.S. Pat. No. 4,839,465, EP-A-101929, EP-A-333174, EP-A-336230, EP-A-394989, EP-A-443132, EP-A-498069, EP-A-515681, EP-A-517589, WO-A-92/22569 and GB-A-2216529 may also be used in the invention as substance P antagonist peptide.

The non-peptide substance P antagonists which can be used in the invention are, in particular, compounds comprising a nitrogen atom linked directly or indirectly to a benzene ring or contained in a heterocycle.

As heterocyclic compound, those described in the following documents can be used in the invention: EP-A-360390, EP-A-429366, EP-A-430771, EP-A-499313, EP-A-514273, EP-A-514274, EP-A-514275, EP-A-514276, EP-A-520555, EP-A-528495, EP-A-532456, EP-A-545478, EP-A-558156, WO-A-90/05525, WO-A-90/05729, WO-A-91/18878, WO-A-91/18899, WO-A-92/12151, WO-A-92/15585, WO-A-92/17449, WO-A-92/20676, WO-A-93/00330, WO-A-93/00331, WO-A-93/01159, WO-A-93/01169, WO-A-93/01170, WO-A-93/06099, WO-A-93/09116. In particular, the compound comprising at least one nitrogenous heterocycle is a 2-tricyclyl-2-aminoethane derivative, a spirolactam derivative, a quinuclidine derivative, an azacyclic derivative, an aminopyrrolidine derivative, a piperidine derivative, an aminoazaheterocycle or an isoindole derivative.

As compounds containing a nitrogen atom linked directly or indirectly to a benzene ring, mention may be made of those described in the following documents: EP-A-522,808 and WO-A-93/01165.

The salts of the elements of column II A of the Periodic Table which can be used in the invention may be beryllium salts or salts of alkaline-earth metals, in particular of strontium, barium or magnesium. This salt is advantageously a strontium salt.

The extracts of bacterial origin which can be used in the invention may be extracts of at least one non-photosynthetic filamentous bacterium.

As extract of plant origin which can be used in the invention, mention may be made in particular of those derived from *Iris germanica, Iris florentina, Iris pallida, Crocus versicolor, Romulea bulbucodium* or *Gladiolus communis*. More particularly according to the invention, a plant extract obtained from an Iridaceae is used, and preferably from the plant material of *Iris pallida*. Any extraction method known to those skilled in the art may be used to prepare the extract contained in the composition according to the invention. Mention may be made in particular of alcoholic extracts, in particular ethanolic or aqueous-alcoholic extracts. An extract prepared by the method described in French patent application No. 95/02379 filed by the Applicant may also be used.

In the compositions according to the invention, the substance P antagonist is preferably used in an amount ranging from 0.000001 to 30% by weight relative to the total weight of the composition, and in particular in an amount ranging from 0.0001 to 10% by weight relative to the total weight of the composition.

The substance P antagonist acts essentially on dyes which have an irritant effect, in particular oxidation dyes, non-irritant dyes moreover being present in the composition according to the invention in order to achieve the desired shades.

The direct dyes which can be used according to the invention are chosen from the direct dyes conventionally used for the direct dyeing of keratin fibres. Among these dyes, mention may be made, by way of example, of nitro derivatives of the benzene series, azo dyes, anthraquinone dyes, indamines, indoanilines and indophenols, acidic dyes such as those referred to in the Color Index 3rd edition and natural dyes such as Lawsone. These direct dyes may optionally carry sulphonic or cationic groups so as to improve their solubility in the medium used for the dyeing.

The pigments which can be used according to the invention may be chosen from inorganic or organic pigments conventionally used in cosmetics.

Among the inorganic pigments which may be mentioned, by way of example, are titanium dioxide (rutile or anatase) optionally surface-treated and listed in the Color Index under the reference code CI 77891; black, yellow, red and brown iron oxides, listed under the reference codes CI 77499, 77492 and 77491; manganese violet (CI 77742); ultramarine blue (CI 77007); chromium oxide hydrate (CI 77289); ferric blue (CI 77510).

Among the organic pigments which may be mentioned, by way of example, are the pigment yellow 3 sold in particular under the trade name Jaune Covanor W 1603 by the company Wacker (CI 11710), D & C red No. 19 (CI 45170), D & C red No. 9 (CI 15585), D & C red No. 21 (CI 45380), D & C orange No. 4 (Cl 15510), D & C orange No. 5 (CI 45370), D & C red No. 27 (CI 45410), D & C red No. 13 (CI 15630), D & C red No. 7 (CI 15850-1), D & C red No. 6 (CI 15850-2), D & C yellow No. 5 (CI 19140), D & C red No. 36 (CI 12085), D & C orange No. 10 (CI 45425), D & C yellow No. 6 (CI 15985), D & C red No. 30 (CI 73360), D & C red No. 3 (CI 45430), carbon black (CI 77266), and lakes based on cochineal carmine (CI 75470).

Pearlescent pigments may also be used, which may be chosen in particular from white pearlescent pigments such as mica coated with titanium oxide or bismuth oxide; coloured pearlescent pigments such as titanium mica with iron oxides, titanium mica with ferric blue or chromium oxide, titanium mica with an organic pigment of precipitated type, as well as those based on bismuth oxychloride.

The oxidation dye precursors which can be used according to the invention in the compositions intended for oxidation dyeing are known per se. Reference may be made more particularly to ZVIAK, Sciences des traitements capillaires [Hair treatment science] 1988, pages 235 to 287. These are, more particularly, diamines or aminophenols containing amino and hydroxyl functional groups in an ortho or para position. These oxidation dye precursors, also known as oxidation bases, are colourless or weakly coloured compounds which, when mixed with oxidizing products at the time of use, may give rise to coloured compounds and dyes by a process of oxidative condensation.

It is also known that the shades obtained with these oxidation bases can be varied by combining them with couplers or colour modifiers, chosen in particular from aromatic meta-diamines, meta-aminophenols and meta-diphenols.

The dye compositions may also contain indole precursors which generate pigments of melanin type under the action of an oxidizing agent. These indole precursors may constitute an oxidation base or a coupler, depending on the case. These indole precursors are more particularly described in French patents and patent applications FR-A-2,593,061, 2,593,062, 2,595,245, 2,606,636, 2,636,237 and European patent applications EP-A-425,345 and EP-A-424,261. The preferred indole precursors are chosen from 5,6-dihydroxyindole and derivatives thereof and 6- and 7-monohydroxyindoles.

The medium which is suitable for dyeing (or support) for the composition is generally an aqueous medium consisting of water or a mixture of water and at least one organic solvent used to solubilize the compounds which would not be sufficiently water-soluble.

Among these solvents which may be mentioned, by way of example, are $C_1$–$C_4$ lower alkanols such as ethanol and isopropanol; glycerol; glycols and glycol ethers such as 2-butoxyethanol, propylene glycol, propylene glycol monomethyl ether, and diethylene glycol monoethyl ether and monomethyl ether; as well as aromatic alcohols such as benzyl alcohol or phenoxyethanol; similar products and mixtures thereof.

When they are present, the solvents preferably represent 1 to 50% by weight relative to the total weight of the dye composition, and even more preferably from 5 to 30% by weight.

The substance P antagonist also allows the irritant effect of some of these solvents to be reduced.

The dye compositions in accordance with the invention may also contain various adjuvants used conventionally in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, packaging agents, film-forming agents, preserving agents, opacifiers and sunscreens.

The pH of the composition applied to the hair is preferably between 3 and 11. It is adjusted to the desired value using basifying agents conventionally used in the dyeing of keratin fibres, such as aqueous ammonia, alkaline carbonates, alkanolamines such as, for example, mono-, di- and triethanolamines and derivatives thereof, sodium hydroxide or potassium hydroxide, or by means of conventional acidifying agents, for instance inorganic or organic acids such as, for example, hydrochloric acid, tartaric acid, citric acid, lactic acid and orthophosphoric acid.

The dye compositions in accordance with the invention may be in various forms, such as in the form of liquids, creams, gels or any other form which is suitable for dyeing keratin fibres, and in particular human hair.

When the dye compositions are used for oxidation dyeing, they are mixed at the time of use with a composition containing, in a medium which is suitable for dyeing, at least one oxidizing agent.

The oxidizing agent is chosen from the oxidizing agents used conventionally in oxidation dyeing and preferably from hydrogen peroxide, urea peroxide, alkali metal bromates, and persalts such as perborates and persulphates. Hydrogen peroxide is particularly preferred.

The pH of the oxidizing composition is such that, after mixing with the dye composition, the pH of the resulting composition applied to the keratin fibres is preferably between 3 and 11. It is adjusted to the desired value using acidifying agents or, optionally, basifying agents which are well known in the state of the art, such as those described above.

The mixture of the dye composition and the oxidizing composition is then applied to the keratin fibres under the same conditions as above.

The amounts of the various constituents of the compositions according to the invention are those used conventionally in the fields considered.

The examples which follow are intended to illustrate the invention without, however, limiting the scope thereof.

EXAMPLE 1

Oxidation dye composition para-phenylenediamine 0.4 g 4-hydroxyindole 0.1 g resorcinol (additional coupler) 0.3 g strontium chloride 5 g oleyl alcohol polyglycerolated with 2 mol of glycerol 4 g oleyl alcohol polyglycerolated with 4 mol of glycerol, containing 78% active material (AM) 5.69 g AM oleic acid 3 g oleylamine containing 2 mol of ethylene oxide, sold under the trade name Ethomeen O12 by the company Akzo 7 g diethylaminopropyl laurylaminosuccinamate sodium salt, containing 55% AM 3 g AM oleyl alcohol 5 g oleic acid diethanolamide 12 g propylene glycol 3.5 g ethyl alcohol 7 g dipropylene glycol 0.5 g propylene glycol monomethyl ether 9 g aqueous sodium metabisulphite solution containing 35% AM 0.455 g AM ammonium acetate 0.8 g antioxidant, sequestering agent qs fragrance, preserving agent qs aqueous ammonia containing 20% $NH_3$ 10 g water qs 100 g At the time of use, the composition obtained is mixed with an equal amount of a composition consisting of 20-volumes aqueous hydrogen peroxide solution (6% by weight).

EXAMPLE 2

The same composition as in Example 1 was prepared, replacing the 5 g of strontium chloride with 0.05 g of Spantide II.

EXAMPLE 3

The same composition as in Example 1 was prepared, replacing the 5 g of strontium chloride with 5 g of an extract of Iris pallida prepared as follows:

Undifferentiated cells of *Iris pallida* cultivated in vitro under axenic conditions are recovered after culturing in a conical flask or in a fermenter by filtration through a 50 µm sieve. To 55 g of fresh material thus obtained are added 27.5 ml of demineralized water. The mixture is ground with a Turrax machine at 24,000 rpm for 1 minute at 4° C. (ice bath). The grindings are centrifuged at 4° C. The supernatant is filtered through a 0.22 µm filter (sterilizing filtration). The extract thus prepared is stored at 4° C. It contains about 15 g solids per liter.

EXAMPLE 4

Dyeing kit

First composition: lotion to be applied before dyeing strontium chloride 7 g ethyl alcohol 10 g water qs 100 g Second composition: dye composition para-phenylenediamine 0.4 g 4-hydroxyindole 0.1 g resorcinol (additional coupler) 0.3 g oleyl alcohol polyglycerolated with 2 mol of glycerol 4 g oleyl alcohol polyglycerolated with 4 mol of glycerol, containing 78% active material (AM) 5.69 g AM oleic acid 3 g oleylamine containing 2 mol of ethylene oxide, sold under the trade name Ethomeen O12 by the company Akzo 7 g diethylaminopropyl laurylaminosuccinamate sodium salt, containing 55% AM 3 g AM oleyl alcohol 5 g oleic acid diethanolamide 12 g propylene glycol 3.5 g ethyl alcohol 7 g dipropylene glycol 0.5 g propylene glycol monomethyl ether 9 g aqueous sodium metabisulphite solution containing 35% AM 0.455 g AM ammonium acetate 0.8 g antioxidant, sequestering agent qs fragrance, preserving agent qs aqueous ammonia containing 20% $NH_3$ 10 g water qs 100 g Firstly, the first composition is applied to the hair and, after an interval of 5 minutes, the dye composition is applied.

What is claimed is:

1. A composition for dyeing keratin fibers containing
   (i) a cosmetically acceptable medium,
   (ii) at least one substance P antagonist which is selected from the group consisting of senside, spantide II, an Iridaceau extract and combinations thereof, and further comprising
   (iii) at least one active agent which exhibits an irritant side effect, wherein said at least one active agent which exhibits an irritant side effect is selected from the group consisting of dyes, pigments, and dye precursors, wherein said active agent is present in an amount effective to dye said keratin fibers, and wherein the amount of the substance P antagonist contained in said composition is sufficient to alleviate or eliminate the irritant side effect of said at least one active agent.

2. A composition suitable for dyeing keratin fibers containing, in a medium suitable for dyeing (i) at least one dye, pigment, or dye precursor which exhibits an irritant side effect, and further comprising (ii) at least one substance P antagonist selected from the group consisting of senside, spantide II, an Iridaceau extract and combinations thereof, wherein said at least one dye, pigment or dye precursor is present in an amount effective to color said keratin fibers, and wherein the amount of said at least one substance P antagonist relative to said dye, pigment or dye precursor is effective to alleviate or eliminate the irritant side effects of said dye, pigment or dye precursor.

3. A composition according to claim 1 or 2, wherein said substance P antagonist is senside or spantide II.

4. A composition according to claim 1 or 2, wherein said substance P antagonist comprises an Iridaceae extract.

5. A composition according to claim 1 or 2, wherein the amount of said substance P antagonist ranges from 0.000001 to 30% by weight relative to the total weight of the composition.

6. A composition according to claim 1 or 2, wherein the amount of said substance P antagonist ranges from 0.0001 to 10% by weight relative to the total weight of the composition.

7. A composition according to claim 1 or 2, wherein said dye is a direct dye.

8. A composition according to claim 7, wherein said direct dye is selected from the group consisting of nitro derivatives of the benzene series, azo dyes, anthraquinone dyes, indamines, indoanilines, indophenols, acidic dyes and natural dyes.

9. A composition according to claim 1 or 2, wherein said pigment is selected from the group consisting of inorganic, organic and pearlescent pigments.

10. A composition according to claim 1 or 2, wherein said dye precursor is selected from the group consisting of diamines and aminophenols containing amino and hydroxyl functional groups in the ortho or para position.

11. A composition according to claim 1 or 2, which is suitable for oxidation dyeing and which composition further comprises at least one coupler selected from the group consisting of aromatic meta-diamines, meta-aminophenols and meta-diphenols.

12. A composition according to claim 1 or 2, which is suitable for oxidation dyeing and which composition comprises at least one indole precursor.

13. A composition according to claim 12, wherein said indole precursor is selected from the group consisting of 5,6-dihydroxyindole, derivatives thereof and 6- and 7-monohydroxyindoles.

14. A composition according to claim 1 or 2, wherein said medium comprises an aqueous medium or a mixture of water and inorganic solvent.

15. A composition according to claim 1 or 2, wherein said composition further comprises at least one adjuvant selected from the group consisting of surfactants, polymers, thickeners, antioxidants, penetration agents, sequestering agents, fragrances, buffers, dispersing agents, packaging agents, film-forming agents, preserving agents, opacifiers and sunscreens.

16. A combination suitable for dyeing keratin fibers which comprises (i) a first composition comprising at least one substance P antagonist selected from the group consisting of senside, spantide II, an Iridaceau extract and combinations thereof and (ii) a second composition which comprises a medium suitable for dyeing, and further comprises at least one dye, pigment or dye precursor which exhibits an irritant side effect and which is present in an amount effective to dye said keratin fibers, wherein said two compositions are suitable for combined usage in dyeing keratin fibers, when said compositions are applied sequentially in a dyeing process, and wherein the amount of said at least one substance P antagonist contained in the first composition is sufficient to alleviate or eliminate the irritant side effects of said at least one dye, pigment or dye precursor contained in said second composition.

17. A process for dyeing keratin fibers which process comprises applying to keratin fibers
  (i) a first composition containing at least one substance P antagonist selected from the group consisting of neodymium salts, bacterial extracts, senside, spantide II, an Iridaceau extract and combinations thereof, and thereafter applying
  (ii) a second composition which comprises at least one dye, pigment, or dye precursor which exhibits an irritant side effect and which is contained in a medium which is suitable for dyeing, wherein the amount of said second composition which is supplied is sufficient to dye said keratin fibers, and wherein the amount of said substance P antagonist contained in said first composition is sufficient to alleviate or eliminate the irritant side effect of said dye, pigment or dye precursor contained in said second composition.

18. A process for dyeing keratin fibers which process comprises applying to said keratin fibers a dye composition comprising
  (i) at least one substance P antagonist selected from the group consisting of neodymium salts, bacterial extracts, senside, spantide II, an Iridaceau extract and combinations thereof, and
  (ii) an effective dyeing amount of at least one dye, pigment or dye precursor which exhibits an irritant side effect,
  wherein said at least one substance P antagonist and dye, pigment or dye precursor are comprised in a medium which is suitable for dyeing, and wherein the amount of said at least one substance P antagonist is sufficient to alleviate or eliminate the irritant side effect of said at least one dye, pigment or dye precursor.

19. A process according to claim 18, wherein said dye composition is mixed with an oxidizing composition before application to said keratin fibers.

20. A process according to claim 18 or 19, wherein said substance P antagonist is an Iridaceae extract.

21. A kit suitable for dyeing keratin fibers which comprises (i) a first composition containing at least one substance P antagonist selected from the group consisting of senside, spantide II, an Iridaceau extract and combinations thereof, and (ii) a second composition containing, in a medium suitable for dyeing, at least one dye, pigment, or dye precursor which exhibits an irritant side effect and which is present in an amount sufficient to dye said keratin fibers, wherein said two compositions are packaged separately, thereby enabling such compositions to be applied sequentially to keratin fibers in a dyeing process, and wherein the amount of said substance P antagonist contained in said first composition is sufficient to alleviate or eliminate the irritant side effect of said at least one dye, pigment or dye precursor contained in said second composition.

* * * * *